United States Patent
Wang et al.

(10) Patent No.: US 6,478,814 B2
(45) Date of Patent: Nov. 12, 2002

(54) STENT SECUREMENT SLEEVES AND OPTIONAL COATINGS AND METHODS OF USE

(75) Inventors: Lixiao Wang, Maple Grove, MN (US); John Jianhua Chen, Plymouth, MN (US); The Thomas Trinh Tran, Coon Rapids, MN (US); Jon St. Germain, Elk River, MN (US); David J. Blaeser, Champlin, MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/407,836

(22) Filed: Sep. 28, 1999

(65) Prior Publication Data

US 2001/0032008 A1 Oct. 18, 2001

Related U.S. Application Data

(63) Continuation-in-part of application No. 09/332,914, filed on Jan. 14, 1999, now Pat. No. 6,168,617.

(51) Int. Cl.[7] .................................................. A61F 2/06
(52) U.S. Cl. ..................................................... 623/1.12
(58) Field of Search ............................... 623/1.1, 1.12, 623/1.44, 1.45, 1.11; 606/108, 198, 191, 192, 194, 428

(56) References Cited

U.S. PATENT DOCUMENTS

| | | | |
|---|---|---|---|
| 4,187,390 A | 2/1980 | Gore ........................... 174/102 |
| 4,346,698 A | 8/1982 | Hanson et al. .................. 128/1 |
| 4,777,951 A | 10/1988 | Cribier et al. ............... 128/344 |
| 4,876,126 A * | 10/1989 | Takemura et al. ........... 428/35.7 |
| 4,877,661 A | 10/1989 | House et al. ................ 428/34.9 |
| 4,896,670 A | 1/1990 | Crittenden ................... 606/194 |
| 4,921,483 A | 5/1990 | Wijay et al. ................... 604/96 |
| 4,950,227 A * | 8/1990 | Savin et al. ................. 606/192 |
| 5,015,231 A | 5/1991 | Keith et al. .................... 604/96 |
| 5,026,513 A | 6/1991 | House et al. ................. 264/127 |
| 5,049,132 A | 9/1991 | Shaffer et al. ............... 604/101 |
| 5,108,416 A * | 4/1992 | Ryan et al. .................. 606/194 |
| 5,338,298 A | 8/1994 | McIntyre ...................... 604/96 |
| 5,415,635 A | 5/1995 | Bagaoisan et al. ............ 604/96 |
| 5,437,632 A | 8/1995 | Engelson ...................... 604/53 |
| 5,470,313 A | 11/1995 | Crocker et al. ............... 604/96 |
| 5,556,414 A * | 9/1996 | Turi .......................... 606/198 |
| 5,643,278 A | 7/1997 | Wijay ......................... 606/108 |
| 5,645,560 A | 7/1997 | Corcker et al. ............. 606/192 |
| 5,670,558 A | 9/1997 | Onishi et al. ................ 523/112 |
| 5,693,085 A * | 12/1997 | Buirge et al. .................. 623/1 |
| 5,749,851 A * | 5/1998 | Wang ........................... 604/96 |
| 5,752,934 A | 5/1998 | Campbell et al. ............. 604/96 |
| 5,800,517 A * | 9/1998 | Anderson et al. ............... 623/1 |
| 5,810,871 A | 9/1998 | Tuckey et al. ............... 606/198 |

(List continued on next page.)

FOREIGN PATENT DOCUMENTS

WO 98/07390 2/1998

*Primary Examiner*—Michael H. Thaler
(74) *Attorney, Agent, or Firm*—Vidas, Arrett & Steinkraus PA

(57) ABSTRACT

A stent delivery system which has a catheter including an inflatable portion. A stent being disposed about the inflatable portion of the catheter, the stent having a contracted state and an expanded state. A pair of stent retaining sleeves which are partially composed of PTFE, each sleeve having a first end portion overlying a respective end of the stent, each sleeve having a second end portion respectively attached to the catheter, the sleeves retaining the stent to the catheter when the stent is in the contracted state, the stent being freed from the sleeves when the stent is placed in the expanded state. The sleeves being placed on the stent by heat shrinking. The inflatable portion of the balloon optionally having stepped compliant characteristics.

25 Claims, 3 Drawing Sheets

U.S. PATENT DOCUMENTS

| | | | |
|---|---|---|---|
| 5,836,965 A | 11/1998 | Jendersee et al. | 606/198 |
| 5,843,116 A | 12/1998 | Crocker et al. | 606/192 |
| 5,902,631 A * | 5/1999 | Wang et al. | 604/265 |
| 5,935,135 A | 8/1999 | Bramfitt et al. | 606/108 |
| 5,944,726 A | 8/1999 | Blaeser et al. | 606/108 |
| 5,968,069 A * | 10/1999 | Dusbabek et al. | 606/194 |
| 5,989,280 A * | 11/1999 | Euteneuer et al. | 623/1 |
| 6,027,517 A | 2/2000 | Crocker et al. | 606/192 |
| 6,120,523 A | 9/2000 | Crocker et al. | 606/192 |
| 6,126,634 A | 10/2000 | Bagaoisan et al. | 604/96 |
| 6,168,617 B1 * | 1/2001 | Blaeser et al. | 623/1.11 |

* cited by examiner

STENT SECUREMENT SLEEVES AND OPTIONAL COATINGS AND METHODS OF USE

CROSS-REFERENCE TO RELATED APPLICATIONS

This application is a Continuation-in-part application from Ser. No. 09/332,914, filed Jan. 14, 1999, now U.S. Pat. No. 6,168,617.

STATEMENT REGARDING FEDERALLY SPONSORED RESEARCH

Not Applicable

BACKGROUND OF THE INVENTION

This invention relates to a medical device delivery systems. More particularly the present invention is directed to stent delivery systems which employ stent retaining sleeves which retain the stent to the catheter prior to delivery of the stent into a body vessel. The present invention provides for a stent delivery system wherein the stent retaining sleeves are composed at least partially of a film of expanded or skived polytetrafluoroethylene (hereinafter PTFE). Other inventive aspects of the present delivery system will be made apparent below.

Stents and stent delivery assemblies are utilized in a number of medical procedures and situations, and as such their structure and function are well known. A stent is a generally cylindrical prosthesis introduced via a catheter into a lumen of a body vessel in a configuration having a generally reduced diameter and then expanded to the diameter of the vessel. In its expanded configuration, the stent supports and reinforces the vessel walls while maintaining the vessel in an open, unobstructed condition.

Both self-expanding and inflation expandable stents are well known and widely available in a variety of designs and configurations. Self-expanding stents must be maintained under positive external pressure in order to maintain their reduced diameter configuration during delivery of the stent to its deployment site. Inflation expandable stents are crimped to their reduced diameter about the delivery catheter, maneuvered to the deployment site, and expanded to the vessel diameter by fluid inflation of a balloon positioned on the delivery catheter. The present invention is particularly concerned with delivery and deployment of inflation expandable stents, although it is generally applicable to self-expanding stents when used with balloon catheters.

In advancing an inflation expandable stent through a body vessel to the deployment site, there are a number of important considerations. The stent must be able to securely maintain its axial position on the delivery catheter, without translocating proximally or distally, and especially without becoming separated from the catheter. The stent, particularly its distal and proximal ends, must be protected to prevent distortion of the stent and to prevent abrasion and/or reduce trauma of the vessel walls.

Inflation expandable stent delivery and deployment assemblies are known which utilize restraining means that overlie the stent during delivery. U.S. Pat. No. 4,950,227 to Savin et al, relates to an expandable stent delivery system in which a sleeve overlaps the distal or proximal margin (or both) of the stent during delivery. During expansion of the stent at the deployment site, the stent margins are freed of the protective sleeve(s). U.S. Pat. No. 5,403,341 to Solar, relates to a stent delivery and deployment assembly which uses retaining sheaths positioned about opposite ends of the compressed stent. The retaining sheaths of Solar are adapted to tear under pressure as the stent is radially expanded, thus releasing the stent from engagement with the sheaths. U.S. Pat. No. 5,108,416 to Ryan et al., describes a stent introducer system which uses one or two flexible end caps and an annular socket surrounding the balloon to position the stent during introduction to the deployment site.

As previously stated, the present invention is particularly concerned with the delivery and deployment of inflation expandable stents. As such, the present invention is also directed to stent delivery catheters which have an expandable portion(s) or balloon(s), wherein the balloon may have a stepped compliance curve. In a preferred embodiment of the invention the stent delivery system employs a balloon which has a portion or portions which are characterized as having a stepped compliance curve and other portion or portions which have a linear compliance curve to burst pressure. In the embodiment where the balloon has a stepped compliant portion any sleeve material may be used. An example of sleeves which may be used with a stepped compliant balloon according to the present invention are disclosed in U.S. Pat. No. 4,950,227 to Savin et al, the entire contents of which is hereby incorporated by reference.

An example of a balloon having the preferred stepped compliant characteristics described above is disclosed in U.S. Pat. No. 5,749,851 to Wang. U.S. Pat. Nos. 5,843,116 and 5,645,560 to Crocker et al. The Crocker et al. references describe balloons which may also be used with the preferred embodiment of the stent delivery system as described above.

The entire content of all of the patents listed within the present patent application are incorporated herein by reference.

BRIEF SUMMARY OF THE INVENTION

This invention provides for a stent delivery system which includes a catheter, a stent mounting region, a stent mounted thereupon, and one or more stent retaining sleeves. The stent mounting region may be located about a balloon or inflatable portion of the catheter. A stent which is mounted to the stent mounting region may be self-expanding, such as a NITINOL shape memory stent, or it may be expandable by means of the expandable portion of the catheter or balloon. The stent is held in place around the stent mounting region prior to percutaneous delivery of the stent by means of one and preferably two end sleeves which are composed, at least partially of a film of PTFE.

The end sleeves may be solid tubes of extruded and shaped PTFE; a tube of PTFE and any thermoplastic elastomer material in combination; or a sectionally diverse tube having portions which are exclusively PTFE, thermoplastic polymer(s), or any combination thereof. In a preferred embodiment, a combination PTFE and thermoplastic elastomer sleeves may be heat shrunk to the catheter and stent when the present stent delivery system is in the reduced or predelivery state. In yet another preferred embodiment, the balloon or inflatable portion of the catheter may have one or more portions characterized as being stepped compliant.

BRIEF DESCRIPTION OF THE SEVERAL VIEWS OF THE DRAWINGS

A detailed description of the invention is hereafter described with specific reference being made to the drawings in which.

DETAILED DESCRIPTION OF THE INVENTION

Figure 1:
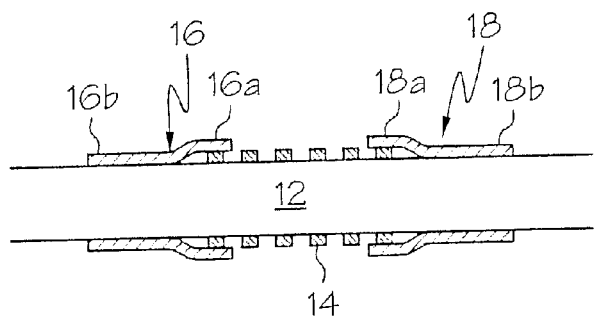
FIG. 1 is a perspective view of an embodiment of the present stent delivery system with PTFE sleeves wherein the inflatable portion of the catheter is in the non-inflated state.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

Figure 2:
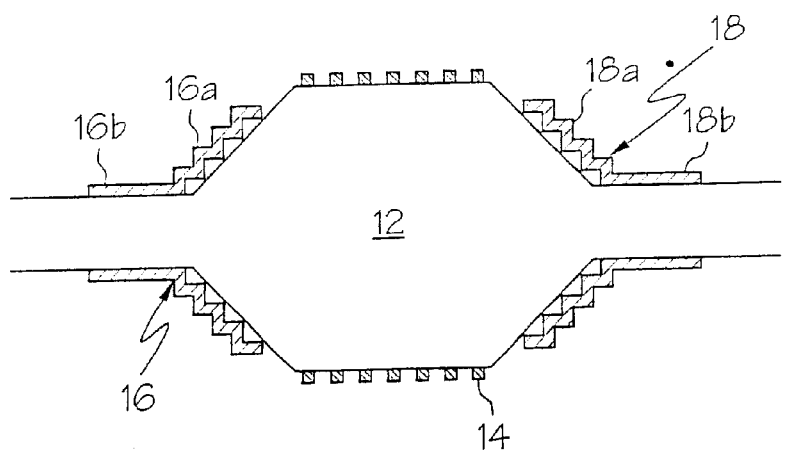
FIG. 2 is a perspective view of an embodiment of the present stent delivery system with PTFE sleeves wherein the inflatable portion of the catheter is in the inflated state.

FIGS. 1 and 2 show an embodiment of the present invention wherein a stent delivery catheter, generally designated 10, has an expandable portion or balloon 12. FIG. 1 shows the expandable portion in its reduced or non-inflated state, whereas FIG. 2 shows the expandable portion in the inflated state. The expandable portion may be an inherent part of the catheter, as shown, or alternatively may be a separate balloon which is affixed to the catheter in any manner which is well known to one of ordinary skill in the art.

Disposed about balloon 12 is a stent 14 as shown. Stent 14 may be any stent type capable of being delivered by a stent delivery catheter. These stents may be self-expanding or balloon expandable.

Attached to the catheter 10 are a pair of sleeves 16, 18. The sleeves each include a first portion 16a, 18a. As shown in FIG. 1, when the balloon 12 is in the non-inflated state first, sleeve portions 16a, 18a overlay the ends of balloon 12 as well as the ends of stent 14. When the balloon 12 is in the inflated state, as shown in FIG. 2, the stent is pushed radially outward by the expanded balloon, causing the stent to be freed from underneath first sleeve portions 16a 18a.

Sleeves 16, 18 also include respective second portions 16b, 18b. Regardless of the state of the balloon 12, non-inflated or inflated, second sleeve portions 16b, 18b are fixedly attached to catheter 10. Preferably, the sleeves each have a thickness within the range of 0.001 to 0.003 inches.

The second sleeve portions may be attached to the catheter utilizing any method of attachment known. However, in a preferred embodiment of the present invention, the sleeves are attached to the catheter and stent by heat shrinking. In this preferred embodiment the sleeves may be composed of PTFE film or PTFE film in combination with other materials, such as one or more thermoplastic elastomers.

Some examples of thermoplastic elastomers which may be used in the present invention include: block copolymers; copolymers and terpolymers of ethylene; homopolymers, copolymers and terpolymers of propylene; ethylene α-olefins; polyurethanes; vinyl copolymers; ionomer materials; polyether-polyester block copolymers; polyether block amide copolymers; polyvinyl chloride; polyetherurethanes; polyesterurethanes; polyurethane ureas; polyurethane siloxane block copolymers; silicone polycarbonate copolymers; ethylene vinyl acetate copolymers; copolyesters or any combinations thereof.

As stated above the present invention is directed to sleeves which utilizes PTFE material which has been expanded or skived. A preferred type of skived PTFE film which may be used in the present invention is commercially obtainable from Dewal Industries Inc. of Saunderstown, R.I. under the name DW/200. Such material comprises a modified PTFE polymer, modified by the addition of a small amount of perfluro propyl vinyl ether (PPVE). It is believed that the addition of PPVE causes the PTFE to be more amorphous and more plasticized than pure crystalline PTFE. Such modification also allows the PTFE film to be heat sealed upon itself.

In the embodiment shown in FIGS. 1 and 2 the sleeves may be composed entirely of PTFE. Such PTFE sleeves have first portions 16a, 18a whose physical characteristics are such that they will tend to draw back in a wrinkled configuration toward second portions 16b, 18b when the balloon 12 is in the inflated state as may be seen in FIG. 2.

It should be appreciated that other PTFE films may be suitably used as may be know or hereafter devised by those skilled in the art. For example, in all embodiments of the present invention the PTFE material used may be a homopolymer or a copolymer with small amounts of fluoro-comonomer. Where the PTFE material is a copolymer, the fluoro-comonomer measures less than 10% of the composition.

In order to attach the sleeves to the catheter by heat shrinking, the PTFE and elastomer are combined together by extrusion or by coating and then formed into thin tubes. Some examples of thermoplastic elastomers which may be heat shrunk include: polyurethane, polycarbonateurethane, polyamide elastomer, polyolefin elastomer and polyester elastomer. The thin tubes are then expanded, at a temperature within the range of approximately 25 degrees Celsius and 70 degrees Celsius. More preferably the tubes are expanded at a temperature of 50 degrees Celsius. The expanded sleeve tubes are then loaded onto the catheter and placed over the ends of the stent. The tubes are then allowed to contract around the catheter and stent at the same temperature at which the tubes were exposed to during expansion. In order to ensure that the sleeves are properly secured to the catheter, the portion of the respective sleeves which overlie the catheter must be attached to the catheter by heat welding, laser welding, adhesive bonding or otherwise. Where the second portion of the sleeves are adhesively bonded to the catheter any adhesive used must bond to both the sleeve material and the catheter. The chemical adhesive may be applied to the tube or the catheter prior to shrinking the tube or after shrinkage has taken place.

In prior stent delivery devices which utilize sleeves, chemical pre-treatment of the sleeve tubes was required in order to properly swell or stretch the sleeve material prior to attaching the sleeves to the delivery catheter. In the present invention, wherein a sleeve tube is at least partially composed of PTFE, the physical character of an appropriate thermoplastic polymer when combined with PTFE provides the sleeve tube with the ability to be stretched and subsequently shrunk in the manner described above, without the need for chemical pretreatment.

Avoiding chemical pre-treatment of the sleeve tube also provides for improved insertion of the tubes onto the catheter and stent. A combination PTFE and thermoplastic elastomer sleeve tube will have a greater range between the pre-shrunk diameter and the heat shrunk diameter, thus providing the inventive tube having a predetermined pre-shrunk diameter with the capability to be heat-shrunk to a wider range of catheter calibers when compared to a prior sleeve tube of the same pre-shrunk diameter but which required chemical pretreatment. The greater range of use of the present invention provides for sleeves tube that may be manufactured with greater efficiency than prior sleeves by avoiding the need of having sleeve tubes with a wide variety of pre-shrunk diameters.

As previously stated, in the embodiment shown in FIGS. 1 and 2, sleeves 16, 18 may be composed entirely of PTFE. However, sleeves 16, 18, or portions thereof, may also be composed of PTFE which is interconnected with other non-PTFE material or materials. Such an interconnection of PTFE and non-PTFE materials is made possible due to the fibrous nature of PTFE. It is known that the types of PTFE to which the present invention is concerned with, namely expanded or stretched skived PTFE, has a node-fibril structure, wherein individual PTFE fibers may have spaces or gaps therebetween. PTFE may be joined with other materials such as, thermoplastic elastomers, by filling the gaps between the PTFE fibers with the thermoplastic polymer. Such an interconnection allows the present sleeves to have a variety of structural components which may be joined to the PTFE material. For numerous reasons relating to manufacturability, cost, strength of the sleeves, bonding characteristics of the sleeves, etc, it may be desirable to utilize the fibrous structure of PTFE in order to combine PTFE material with one or more thermoplastic elastomers in the manner described.

Figure 5:
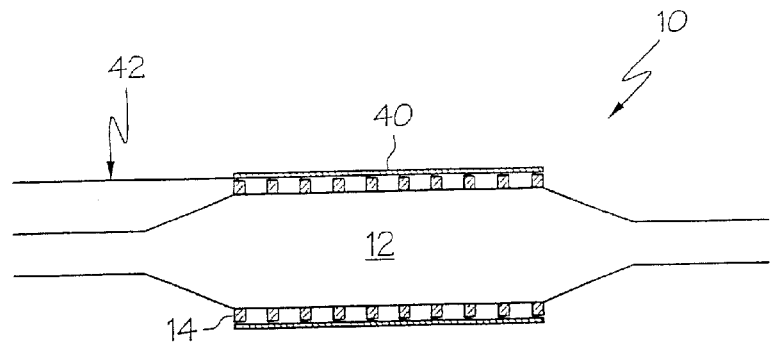
FIG. 5 is a perspective view of an embodiment of the present stent delivery system with a stent retaining pullback sleeve and pullback member wherein the sleeve is composed of PTFE.

In an alternative embodiment shown in FIG. 5, the stent delivery system may retain the stent on the catheter utilizing a pullback sheath 40 equipped with a pullback member 42. The pullback sheath 40 may be PTFE or a PTFE and thermoplastic elastomer combination as described above. The pullback member or wire is operatively connected to the sheath 40 at the distal end of the pullback member. The pullback member extends proximally away from sheath 40 and may be manipulated from outside the lumen into which the stent delivery system was inserted.

In the embodiment shown in FIG. 5, the stent 14 is preferably a self-expanding stent as described above. Where a self-expanding stent is used it may be desirable to avoid the use of a balloon or inflatable portion. However, inflatable portion 12 may be useful in seating the stent after the stent has been released and expanded. The stent is released when the pullback member 42 is drawn proximally away from stent 14, thereby pulling the sheath 40 off of the stent.

Sheath 40 may be attached to catheter 10 through any method known. However, in the preferred embodiment of the invention the sheath is attached to the catheter using the heat shrinking method described above.

Returning now to the embodiment of the invention wherein a pair of sleeves are used to retain the stent on the catheter, it may also be desirable to utilize PTFE material exclusively on certain portions of the sleeves. For example, in order to ensure proper release of the stent from the catheter during balloon expansion, the sleeve portions which overlie the ends of the stent may preferably be composed of PTFE material. In such an embodiment it may be desirable to have the remaining sleeve portions be composed of a thermoplastic elastomer material or a combination thereof. In the embodiment shown in FIGS. 3 and 4, the sleeves employ a central layer of PTFE which is entirely covered by an outside layer of thermoplastic elastomer material and partially covered by an inside layer of thermoplastic material. In the unique configuration shown only the stent is in contact with the portion of the sleeve which is composed of PTFE material.

Figure 3:
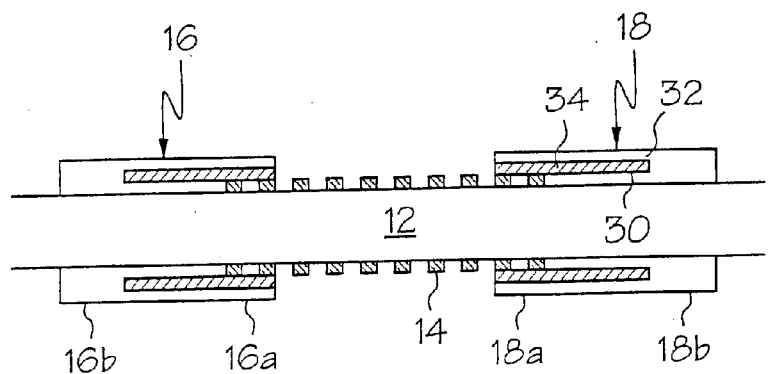
FIG. 3 is a perspective view of an embodiment of the present stent delivery system with sleeves which are composed of non-PTFE outer portions and a PTFE middle portion wherein the inflatable portion of the catheter is in the non-inflated state.
Figure 4:
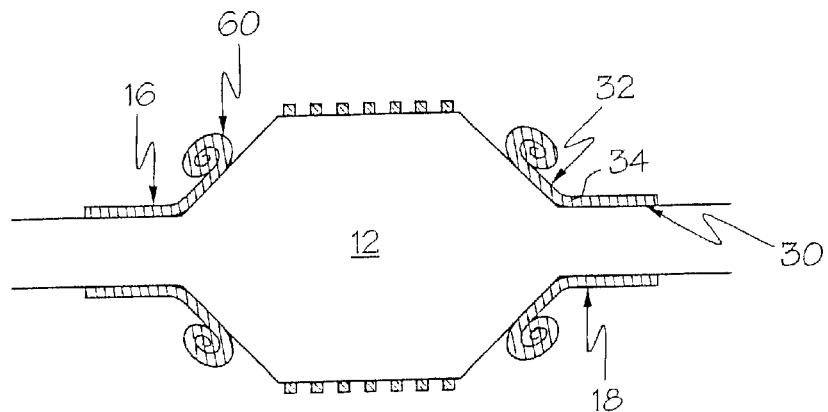
FIG. 4 is a perspective view of the stent delivery system shown in FIG. 3 in the inflated state.

FIG. 3 shows the present embodiment of the stent delivery system in the non-inflated state. FIG. 4 shows the present embodiment in the inflated state.

The sleeves shown in FIGS. 3 and 4 have a multi-layer configuration. Second sleeve portions 16b, 18b have three layers, while first sleeve portions 16a, 18a have two layers.

Beginning with second sleeve portions 16b, 18b, the layers may be described as an inner layer 30, an outer layer 32 and a middle layer 34. Middle layer 34 is composed of PTFE and is sandwiched between inner layer 30 and outer layer 32. Inner layer 30 and outer layer 32 may be composed of the same material, or may be composed of different material. In the embodiment shown, inner layer 30 and outer layer 32 may be composed of any thermoplastic elastomer material and are interconnected or bonded in the manner described above or are otherwise attached to middle layer 34. In an additional preferred embodiment, the inner layer may be composed of material which is specifically suited to attachment to the catheter but which may be attached to the outer layer and to the middle layer of PTFE material as well. In yet another embodiment, the outer layer material may have hydrophilic characteristics or be coated with a hydrophilic material.

As best seen in FIG. 3, both outer layer 32 and the middle layer of PTFE material 34 extends from the second sleeve portions 16b, 18b to the first sleeve portions 16a, 18a. In the embodiment discussed above, wherein outer layer 32 is composed of hydrophilic material, outer layer 32 provides the sleeves and stent delivery system with a reduced frictional interface upon insertion into a body lumen.

Some examples of suitable hydrophilic materials which may be utilized to coat the sleeve surfaces include polyethylene oxide and its copolymers; polyvinylpyrrolidone and its derivatives; polyacrylate, polyacrylic acid, polyacrylamide, polyethylene maleic anhydride and their derivatives.

A sleeve which has a PTFE middle layer 34 and non-PTFE layers 30, 32 as described above, will have inner and outer surface characteristics which will attract one another. As a result the sleeve will tend to roll back upon themselves when the balloon 12 is placed in the inflated state as may best be seen in FIG. 4. This provides for an improved sleeve configuration which helps to ensure more uniform and complete release of the stent.

Figure 6:
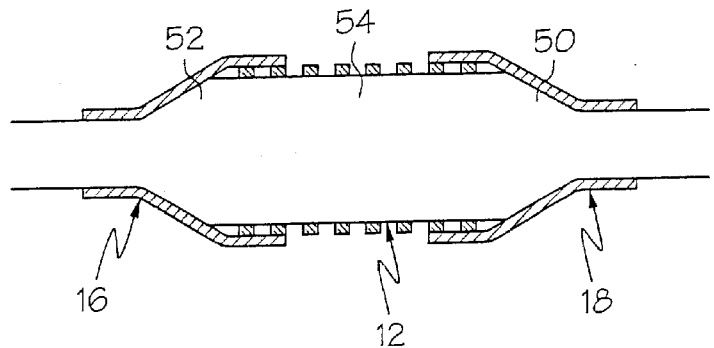
FIG. 6 is a perspective view of an embodiment of the present stent delivery system which has an inflatable portion shown in the non-inflated state, the inflatable portion having ends which have a stepped compliance curve.
Figure 7:
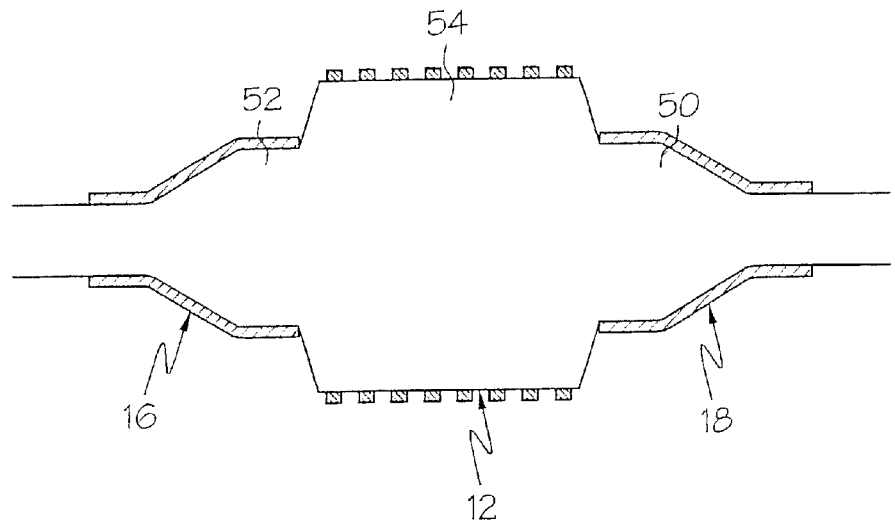
FIG. 7 is a perspective view of the embodiment of the stent delivery system shown in FIG. 6 in the inflated state.

Turning now to FIGS. 6 and 7, which show a further embodiment of the present invention wherein the stent delivery system utilizes an inflatable portion or balloon having at least some stepped compliant characteristics.

In addition to those already mentioned, stent deployment systems which have stepped compliant balloons are also described in U.S. Pat. No. 5,749,851 issued May 12, 1998 to Lixiao Wang, the entire contents of which is herein incorporated by reference.

FIG. 6 shows a preferred embodiment of the stent delivery system in the reduced or non-inflated state. As shown the stent delivery system is equipped with a balloon 12 having end portions 50, 52 which have stepped compliant expansion characteristics and a body portion 54 having generally linear expansion characteristics. It should be noted that the balloon 12 may be constructed to be made entirely stepped compliant, or have configurations where portions of the balloon are stepped compliant or linear compliant in proportions other than described or shown. FIG. 7 shows the present embodiment of the stent delivery system in the inflated state.

When the balloon 12 is inflated as shown in FIG. 7, the body portion 54 will expand more rapidly and to a greater diameter than the stepped compliant end portions 50, 52. The stepped compliant end portion 50, 52 expand relatively slowly during inflation. The differing inflation characteristics of balloon 12 allows the stent to be retained by sleeves 16, 18 through out the inflation period, freeing the stent only after the balloon has been fully inflated. This results in a stent delivery system which reduces the possibility of the stent edges damaging the vessel or lumen to which it is being inserted.

It should be understood that in the embodiment shown in FIGS. 6 and 7, that the sleeves 16, 18 may be composed of materials which include but are not limited to PTFE, or a combination of PTFE and other materials.

Figure 8:
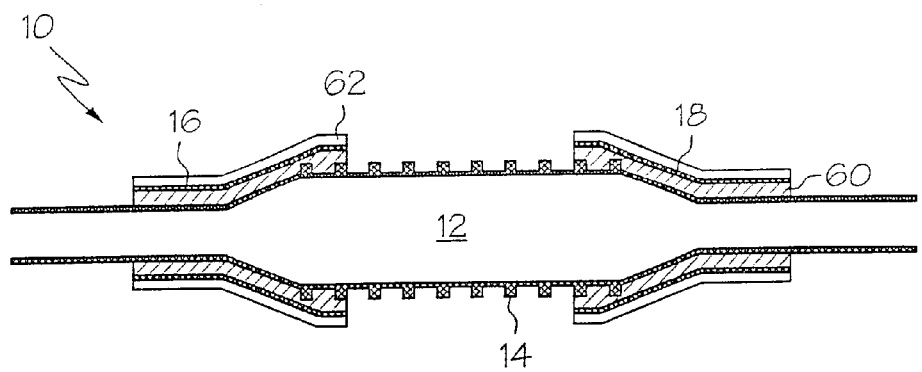
FIG. 8 is a perspective view of a further embodiment of the present stent delivery system wherein the sleeves are coated.

Yet another embodiment of the present stent delivery system is shown in FIG. 8. In the embodiment shown, the inflatable portion 12 is shown in the non-inflated state. Sleeves 16 and 18 are preferably single layer tubes of any suitable thermoplastic elastomer such as CARBOTHANE® from Thermedics Inc. or CHRONOFLEX® from CT Biomaterials. Sleeves 16, 18 have coatings on their inside surfaces and on their outside surfaces. The inside surface coating 60 is may be a coating of any hydrophobic material. The outside surface coating 62 is preferably a coating of hydrophilic material, but a hydrophobic material may also be utilized. Some examples of suitable coatings which may be utilized with the present invention are described in U.S. patent application Ser. No.: 08/740,727, filed with the U.S. Patent and Trademark Office on Nov. 1, 1996 and entitled Selective Coating of a Balloon Catheter with Lubricious Material for Stent Development, the entire contents of which is incorporated by reference. In a preferred embodiment the inside surface coating is composed at least partially, of a layer of PTFE.

Figure 9:
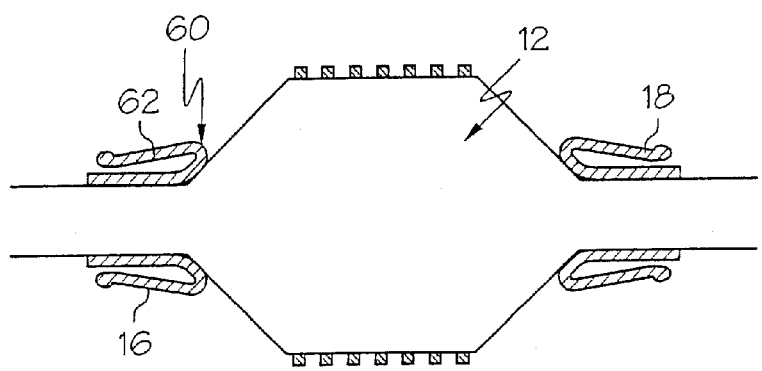
FIG. 9 is a perspective view of an embodiment of the present stent delivery system shown in FIG. 8 wherein the inflatable portion of the catheter is in the inflated state.

FIG. 9 shows the coated sleeves embodiment described above in the inflated state, wherein inside surface coating 60 and outside surface coating 62 are both hydrophobic coatings. As a result of the physical characteristics of the inside and outside hydrophobic coatings, sleeves 16, 18 will tend to roll back upon themselves when the inflatable portion 12 is in the inflated state as shown.

This completes the description of the preferred and alternate embodiments of the invention. Those skilled in the art may recognize other equivalents to the specific embodiment described herein which equivalents are intended to be encompassed by the claims attached hereto.

What is claimed is:

1. A stent delivery system comprising:
   a catheter including an inflatable portion;
   a stent disposed about the inflatable portion of the catheter, the stent having a distal end and a proximal end, the stent further having a contracted state and an expanded state, and
   a pair of stent retaining sleeves which are at least partially composed of PTFE, each sleeve having a first end portion overlying a respective end of the stent, each sleeve having a second end portion respectively attached to the catheter, the sleeves retaining the stent to the catheter when the stent is in the contracted state, the stent being freed from the sleeves when the stent is placed in the expanded state, wherein the stent retaining sleeves are flexible.

2. The stent delivery system of claim 1 wherein the stent retaining sleeves have a composite construction of PTFE material and non-PTFE material.

3. The stent delivery system of claim 2 wherein the non-PTFE material is one or more thermoplastic elastomeric materials.

4. The stent delivery system of claim 3 wherein the one or more thermoplastic elastomeric materials are selected from the group consisting of: block copolymers; copolymers and terpolymers of ethylene; homopolymers, copolymers and terpolymers of propylene; ethylene α-olefins; polyurethanes; vinyl copolymers; ionomer materials, or any combination thereof.

5. The stent delivery system of claim 4 wherein the one or more thermoplastic elastomeric materials are selected from the group consisting of: polyether-polyester block copolymers, polyether block amide copolymers, polyvinyl chloride, polyetherurethanes, polyesterurethanes, polyurethane ureas, polyurethane siloxane block copolymers, silicone polycarbonate copolymers, ethylene vinyl acetate copolymers, copolyesters or any combination thereof.

6. The stent delivery system of claim 3 wherein the PTFE material and the one or more thermoplastic elastomeric materials are interconnected.

7. The stent delivery system of claim 3 wherein a layer of PTFE material is at least partially interconnected with a layer of one or more thermoplastic elastomeric materials, the layer composed of PTFE material at least partially protruding from the one or more thermoplastic elastomeric materials, the layer of PTFE material overlying the stent ends, the layer of one or more thermoplastic elastomeric materials attached to the catheter.

8. The stent delivery system of claim 3 wherein the stent retaining sleeves each have an inside surface and an outside surface, at least a portion of the inside surface composed of PTFE, the outside surface composed of one or more thermoplastic elastomeric materials.

9. The stent delivery system of claim 8 wherein the at least a portion of the inside surface is in contact with the stent when the stent is in the contracted state.

10. The stent delivery portion of claim 1 wherein the inflatable portion has a stepped compliance curve.

11. The stent delivery system of claim 1 wherein the inflatable portion further comprises one or more stepped compliant portions, and at least one linear compliant portion, the one or more stepped compliant portions characterized as having a stepped compliance curve, the at least one linear compliant portion characterized as having a generally linear compliance curve to burst pressure.

12. A stent delivery system comprising:
   a catheter, the catheter having an inflatable section, the inflatable section having a body portion and a pair of end portions, the body portion having a generally linear compliance curve to burst pressure and the end portions respectively having a stepped compliance curve characterized by a low pressure segment defined by a low inflation pressure range, said low pressure segment being generally collinear with a corresponding segment of the compliance curve of the body portion which is defined by said low inflation pressure range, a transition segment during which the inflatable section expands rapidly relative to the body portion and a high pressure segment during which the compliance curve of the end portions expands slowly relative to the transition region;

a stent disposed at least partially about the inflatable section, the stent having a distal end and a proximal end, the stent further having a contracted state and an expanded state, and a pair of stent retaining sleeves, each sleeve having a first end portion overlying a respective end of the stent and an end portion of the inflatable section, each sleeve having a second end portion respectively attached to the catheter, the sleeves retaining the stent to the catheter when the stent is in the contracted state, the stent being freed from the sleeves when the stent is placed in the expanded state, wherein the pair of stent retaining sleeves are at least partially composed of PTFE, wherein the stent retaining sleeves have a composite construction of PTFE material and non-PTFE material and are flexible.

13. A stent delivery system comprising:

a catheter including a stent mounting region constructed and arranged to carry and release a stent;

a stent disposed about the stent mounting region of the catheter, the stent having a first end and a second end, the stent further having a contracted state and an expanded state, and a pair of stent flexible retaining sleeves, the stent retaining sleeves, being constructed at least partially from PTFE and having an inside surface and an outside surface, the inside surface and the outside surface being coated with a hydrophobic material.

14. The stent delivery system of claim 13, wherein the stent retaining sleeves include a thermoplastic elastomer layer.

15. The stent delivery system of claim 13 wherein the hydrophobic material is selected from the group consisting of: silicone based lubricants, slip agents or a combination thereof.

16. A stent delivery system comprising:

a catheter including a stent mounting region constructed and arranged to carry and release a stent;

a stent disposed about the stent mounting region of the catheter, the stent having a first end and a second end, the stent further having a contracted state and an expanded state, and a pair of stent retaining sleeves, the stent retaining sleeves having an inside surface and an outside surface, the inside surface at least partially coated with a hydrophobic material, the outside surface at least partially coated with a hydrophilic material, each sleeve having a first end portion overlying a respective end of the stent, each sleeve having a second end portion respectively attached to the catheter, the stent being freed from the sleeves when the stent is placed in the expanded state.

17. The stent delivery system of claim 16 wherein the hydrophobic material is selected from the group consisting of: silicone based lubricants, slip agents or a combination thereof.

18. The stent delivery system of claim 16 wherein the hydrophilic material is selected from the group consisting of: polyethylene oxide and its copolymers; polyvinylpyrrolidone and its derivatives; polyacrylate, polyacrylic acid, polyacrylamide, polyethylene maleic anhydride, or any combination thereof.

19. A method of attaching a stent retaining sleeve to a catheter comprising the steps of:

(a) providing a catheter which includes a distal portion constructed and arranged to carry and release a stent, the stent at least partially disposed about the distal portion of the catheter, the stent having a first end and a second end, the stent further having a contracted state and an expanded state;

(b) stretching a stent retaining sleeve having a first end and a second end and comprising at least one thermoplastic elastomer and PTFE material to a predetermined extent, wherein the stent retaining sleeve is flexible;

(c) placing the stent retaining sleeve over the distal portion of the catheter and at least one of the stent ends; and (d) contracting the stent retaining sleeve about the catheter, attaching the first end of the retaining sleeve thereto, and the at least one of the stent ends.

20. The method of attaching a stent retaining sleeve to a catheter of claim 19 wherein the stent retaining sleeve is exposed to a temperature between 25 degrees Celsius and 70 degrees Celsius during the stretching and contracting steps.

21. The method of attaching a stent retaining sleeve to a catheter of claim 19 wherein the stent retaining sleeve is exposed to a temperature of 50 degrees Celsius during the stretching and contracting steps.

22. The method of attaching a stent retaining sleeve to a catheter of claim 19 wherein a stent retaining sleeve is stretched over both of the respective stent ends.

23. The method of attaching a stent retaining sleeve to a catheter of claim 19 wherein the at least one thermoplastic elastomer may be selected from the group consisting of, polyurethane, polycarbonateurethane, polyamide elastomer, polyolefin elastomer and polyester elastomer or any combination thereof.

24. A stent delivery system comprising:

a catheter, the catheter having an inflatable section, the inflatable section having a first inflation state and a second inflation state, the inflatable section having a body region positioned between first and second end regions, the body region and each said end region having a respective diameter in each said inflation state, in the second inflation state the body region diameter being greater than the first and second end region diameters;

an expandable stent disposed at least partially about the inflatable section, the stent having a distal end and a proximal end; and a pair of stent retaining sleeves, in the first inflation state each sleeve having a first end portion overlying a respective end of the stent and one of the end regions of the inflatable section, each sleeve having a second end portion respectively engaged to the catheter adjacent to the inflatable section, the pair of stent retaining sleeves retaining the stent to the catheter when the inflatable section is in the first inflation state, wherein the pair of stent retaining sleeves are at least partially composed of PTFE.

25. The stent delivery system of claim 24 wherein the pair of stent retaining sleeves have a composite construction of PTFE material and non-PTFE material and are flexible.

* * * * *